(12) United States Patent
Dixon et al.

(10) Patent No.: US 11,875,704 B2
(45) Date of Patent: Jan. 16, 2024

(54) NOSE SIMULATOR WITH MULTISAMPLING MODES FOR AIRSTREAM EVALUATION

(71) Applicant: US Govt as represented by Secretary of Air Force, Wright-Patterson AFB, OH (US)

(72) Inventors: Angela R. Dixon, Beavercreek, OH (US); Saber M. Hussain, Beavercreek, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 807 days.

(21) Appl. No.: 16/934,357

(22) Filed: Jul. 21, 2020

(65) Prior Publication Data

US 2021/0027661 A1    Jan. 28, 2021

Related U.S. Application Data

(60) Provisional application No. 63/042,615, filed on Jun. 23, 2020, provisional application No. 62/877,502, filed on Jul. 23, 2019.

(51) Int. Cl.
*G09B 23/30* (2006.01)
*G01P 5/00* (2006.01)
(Continued)

(52) U.S. Cl.
CPC .............. *G09B 23/306* (2013.01); *B01L 9/52* (2013.01); *G01N 33/5005* (2013.01);
(Continued)

(58) Field of Classification Search
CPC ........ G09B 23/28; G09B 23/30; G09B 23/303
See application file for complete search history.

(56) References Cited

U.S. PATENT DOCUMENTS 5,055,052 A    10/1991  Johnsen
5,823,787 A *  10/1998  Gonzalez ............... G09B 23/28
                                                          434/267
(Continued)

FOREIGN PATENT DOCUMENTS

CN           1367381 A      9/2002

OTHER PUBLICATIONS

Sander, Ian M., et al. "Three dimensional printing of X ray computed tomography datasets with multiple materials using open source data processing." Anatomical sciences education 10.4 (2017): 383-391.

(Continued)

*Primary Examiner* — Kurt Fernstrom
(74) *Attorney, Agent, or Firm* — AFMCLO/JAZ; Chastity D. S. Whitaker

(57) ABSTRACT

A nasal simulator includes a three-dimensional (3D) printed nasal cavity within based on diagnostic imagery of a human nasal cavity. The nasal simulator comprising a fan system positioned to mimic air flow through the human nasal cavity. A first probe access bore is formed through the 3D printed nasal cavity to a first location having a first internal contour. An anemometer insert having an outer diameter sized to be slidingly received in and to pneumatically seal the first probe access bore, the anemometer insert having a distal contour that aligns with the first internal contour of the 3D printed nasal cavity, the anemometer insert having a longitudinal bore that is sized to receive a probe of an anemometer to detect characteristics of the air flow through the 3D cavity.

5 Claims, 13 Drawing Sheets

(51) Int. Cl.
    *G01P 5/02*     (2006.01)
    *B01L 9/00*     (2006.01)
    *G01N 33/50*     (2006.01)
    *G09B 23/32*     (2006.01)
    *G09B 23/28*     (2006.01)
    *G09B 23/00*     (2006.01)
    *G09B 23/34*     (2006.01)
    *B33Y 80/00*     (2015.01)

(52) U.S. Cl.
    CPC ............... *G01P 5/001* (2013.01); *G01P 5/02* (2013.01); *G09B 23/00* (2013.01); *G09B 23/288* (2013.01); *G09B 23/30* (2013.01); *G09B 23/32* (2013.01); *G09B 23/34* (2013.01); *B01L 2300/0663* (2013.01); *B33Y 80/00* (2014.12)

(56) References Cited

U.S. PATENT DOCUMENTS

| | | | | |
|---|---|---|---|---|
| 6,296,490 | B1* | 10/2001 | Bowden | G09B 23/288 434/272 |
| 10,181,270 | B1* | 1/2019 | Fuller | G09B 23/30 |
| 11,107,370 | B2* | 8/2021 | Minskoff | G09B 23/30 |
| 11,127,314 | B2* | 9/2021 | Bernal | G09B 23/303 |
| 2011/0045450 | A1* | 2/2011 | Nuttal | G09B 23/30 434/267 |
| 2018/0092547 | A1* | 4/2018 | Tzvieli | A61B 5/0935 |
| 2020/0150110 | A1* | 5/2020 | Kerr | B33Y 10/00 |
| 2022/0051592 | A1* | 2/2022 | Bourouiba | G09B 23/28 |

OTHER PUBLICATIONS

Sander, Ian, et al. "Patient education for endoscopic sinus surgery: preliminary experience using 3D-printed clinical maging data." Journal of functional biomaterials 8.2 (2017): 13.

Li, Chengyu, et al. "Computational modeling and validation of human nasal airflow under various breathing conditions." Journal of biomechanics 64 (2017): 59-68.

* cited by examiner

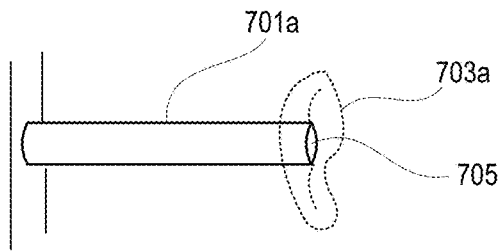
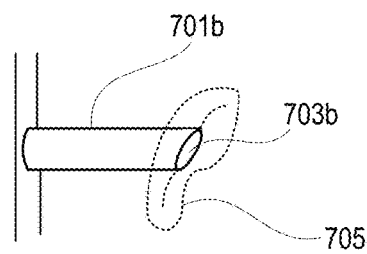
FIG. 7A   FIG. 7B
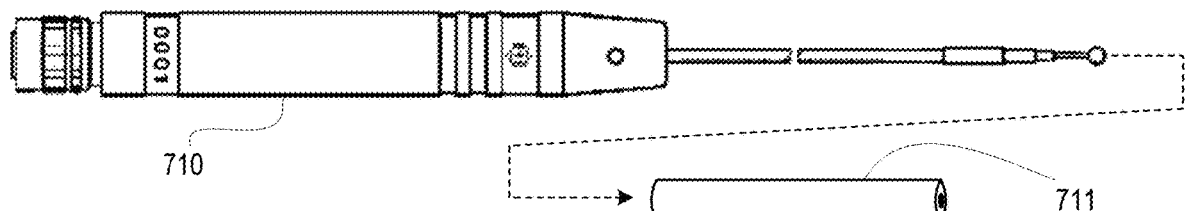
FIG. 7C
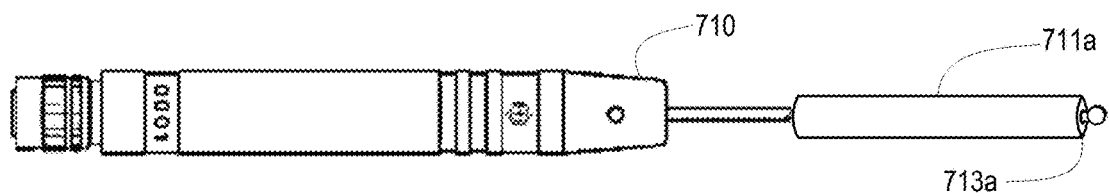
FIG. 7D
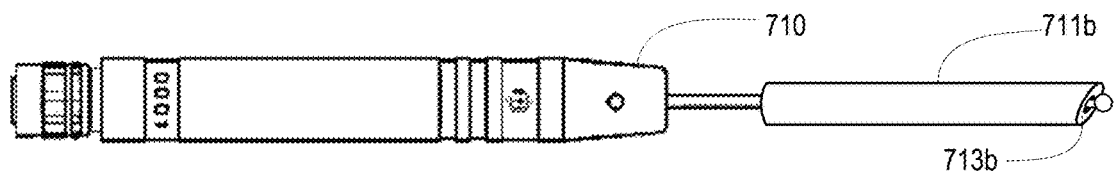
FIG. 7E
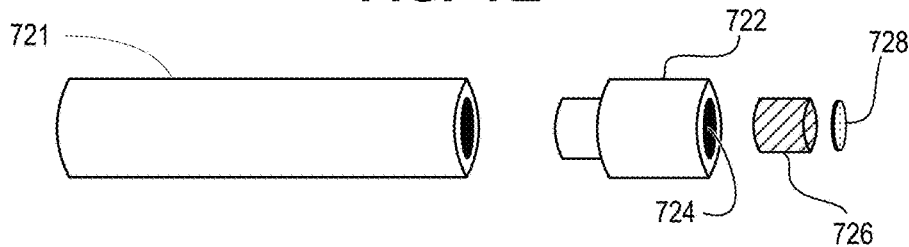
FIG. 7F

NOSE SIMULATOR WITH MULTISAMPLING MODES FOR AIRSTREAM EVALUATION

CROSS-REFERENCE TO RELATED APPLICATIONS

This application claims the benefit of priority under 35 U.S.C. § 119(e) to U.S. Provisional Application Ser. No. 62/877,502 entitled "Nose simulator with multisampling modes for airstream evaluation," filed 23 Jul. 2019, the contents of which are incorporated herein by reference in their entirety.

This application claims the benefit of priority under 35 U.S.C. § 119(e) to U.S. Provisional Application Ser. No. 63/042,615 entitled "Nose simulator with multisampling modes for airstream evaluation," filed 23 Jun. 2020, the contents of which are incorporated herein by reference in their entirety.

ORIGIN OF THE INVENTION

The invention described herein was made by employees of the United States Government and may be manufactured and used by or for the Government of the United States of America for governmental purposes without the payment of any royalties thereon or therefore.

BACKGROUND

1. Technical Field

The present disclosure generally relates to anatomically representative testing apparatuses, and more particularly to nose simulator systems.

2. Description of the Related Art

The air flow and spatial distribution patterns within different regions of the nasal cavity are variable and complex, and more precise environmental monitoring systems that simulate the actual patterned airflow distribution within the nasal cavity are needed to make more realistic and informative evaluations of air quality and the consequential health effects of inhaling different atmospheric compositions.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 7A depicts a side view of a cylindrical rod of a particular length corresponding to a probe access bore and having a perpendicular distal face that aligns with a perpendicular contour at a location of a 3D printed nasal cavity, according to one or more embodiments;

FIG. 7B depicts a side view of a cylindrical rod of a shorter particular length corresponding to a shorter probe access bore and having a non-perpendicular distal face that aligns with a non-perpendicular contour at a location of the 3D printed nasal cavity, according to one or more embodiments;

FIG. 7C depicts an anemometer being inserted through an anemometer insert that was custom design to fit a commercial miniature spherical probe of a flow meter, according to one or more embodiments;

FIG. 7D depicts the anemometer inserted through the anemometer insert of FIG. 7C, according to one or more embodiments;

FIG. 7E depicts the anemometer inserted through an anemometer insert that has a non-perpendicular distal face, according to one or more embodiments;

FIG. 7F depicts a tissue insert having a cylindrical shaft of a length selected to position a tissue holder, according to one or more embodiments;

DETAILED DESCRIPTION

Figure 1:
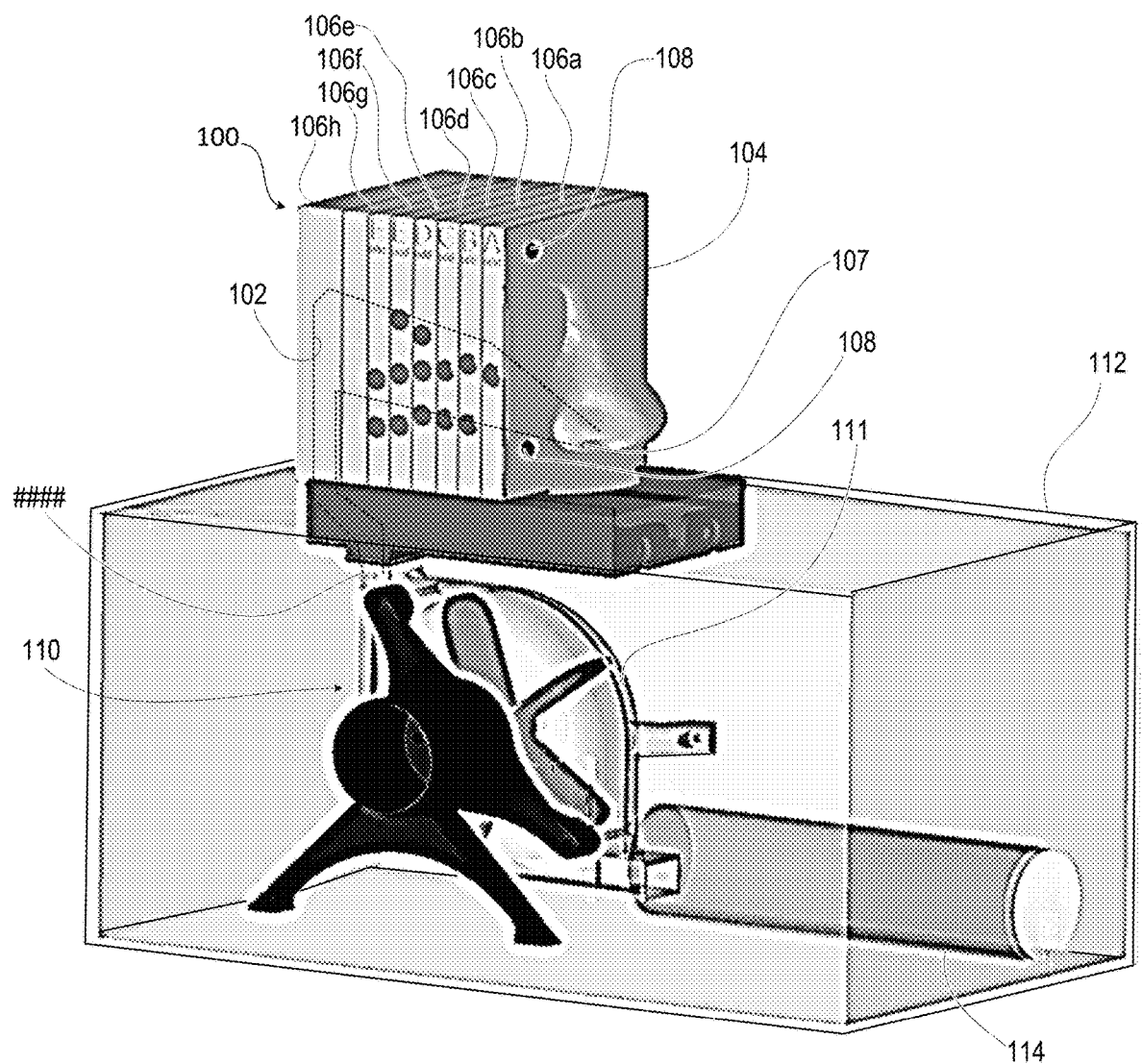
FIG. 1 a three-dimensional (3D) view of a 3D printed breathing human nose simulator for environmental screening and respiratory research, according to one or more embodiments.

According to aspects of the present disclosure, FIG. 1 depicts a three-dimensional (3D) view of a nasal simulator 100 that includes a three-dimensional (3D) printed nasal cavity 102 within a chamber 104 within based on diagnostic imagery of a human nasal cavity. In one or more embodiments, the chamber 104 is sectioned into slides 106a-106h that are compressed together by compression screws 108 that pneumatically sealed the 3D printed nasal cavity 102 that is partially included in each slide 106a-106h, forming an "airlock". Air can bi-directionally move through nostril holes 107 of first slide 106a. The chamber 104 is supported on a sliding track system 108 that enables easy slide securement and manipulation and pharynx-to-fan connection of slide 106g through sliding tracking system 108 to a fan system 110 that mimics bi-directional breathing patterns. A fan 111 of fan system 110 is within a fan container 112 that underlies sliding track system 108 and pneumatically communicates with (vents) ambient air via a compressible exhaust hose 114. Thus, the bi-directional air movement through nostrils 107 corresponds to bi-directional air flow movement through compressible exhaust hose 114. As discussed below, probe access bores 116 are formed through the 3D printed nasal cavity 102 to locations of the 3D printed nasal cavity 102 having a corresponding internal contour. An anemometer insert having an outer diameter sized to be slidingly received in and to pneumatically seal the first probe access bore, the anemometer insert having a distal contour that aligns with the first internal contour of the 3D printed nasal cavity, the anemometer insert having a longitudinal bore that is sized to receive a probe of an anemometer to detect characteristics of the air flow through the 3D cavity 102.

In one or more embodiments, the nasal simulator 100 includes the chamber 104 that provides an upper nasopharynx unit that rests atop the fan container 112 that is an acrylic bottom compartment that houses the fan 111 and electronic hardware. 3D printed transitional structure 118 connects the pharynx portion of the 3D printed nasal cavity 102 to a fan opening of the fan 111 that is centrifugal-like and 3D printed. The fan 111 is driven by a 12V DC moto that is capable of generating bi-directional airflow within the nasal cavity 102.

The nasal simulator enables improved environmental screening and respiratory research. Distribution of airflow within the labyrinth-like geometry of nasal cavity is variable and complex. Few bioengineered systems fully replicate the anatomically and physiological complexity of the upper respiratory system that is required for precise environmental monitoring of air quality and the related effects on respiratory physiology. With the advent of three-dimensional (3D) printing, complex anatomical models can be readily generated from computed tomography (CT) scans of patients. We detail the design of a 3D printable nose simulator that is comprised of a custom bioengineered nasal cast chamber, with anatomically accurate features and autonomous breathing capabilities, which will be ultimately coupled with interchangeable airstream probing modes to sense air velocity, detect inhalant tissue interactions, and map distribution of inhaled particulates.

INTRODUCTION: Inspired air entering the nares travels through a closed labyrinth path shaped by tissue protrusions, called turbinates, which warm, humidify and cleanse air (Mistry et al. 2009). Building a 3D nasal cavity structure that preserves this native anatomical intricacy is challenging and time consuming with commonly-known manufacturing techniques (Hughes et al. 2008). An automated rapid prototyping platform, called 3D printing, or formerly additive manufacturing, is a powerful tool for producing highly complex models in a layer-by-layer process guided by 3D computer aided design data (Hughes et al. 2008). 3D-printing nasal casts have been used for the evaluation of nasal airflow and drug distribution, and also to inform the development of computational models that examine those same parameters (Doody et al. 2008, Zhao et al. 2014, Li et al. 2017). Additionally, 3D printed, human scale models of the nasal cavity, incorporating multiple materials to mimic hard and soft tissue regions, serve as advanced visual-aides and training medical tools for the education of patients and students (Ding et al. 2019, Sander et al. 2017a, Sander et al. 2017b, Zhuo et al. 2019). More accurate and predictive nasal models are needed from predictive research to assay toxic threats or therapeutic benefit. Nasal cast models more closely resemble the nasal cavity architecture and physiological breathing function of humans and cells and tissue permit the evaluation of biological responses resulting from inhalant exposure. All of these machine and biological elements can be fused together to generate innovative function biohybrid systems for various forms of respiratory research. Here we elaborate on our development of a life-size human nasal cavity, with embedded human tissue regions and breathing simulator, as a realistic biohybrid robotic model to conduct more physiological relevant assessments for air quality monitoring, nasal drug discovery development, and classic otolaryngological research.

Primitive processes to fabricate nose models for particle distribution studies involved the use of cadavers to directly cast nasal cavity regions (Mygind and Vesterhauge 1978, Pu et al. 2014, Pozzoli et al. 2016) or to obtain dimensions to guide machining of nasal cavity regions in select materials (Hallworth and Padfield 1986). Glass pieces with simplified geometries were machined based on dimensions of nasal features from cadavers (Hallworth and Padfield 1986). Transparent silicone human nose casts could also be created against positive casts from cadavers (Mygind and Vesterhauge 1978, Pu et al. 2014, Pozzoli et al. 2016)) and these type of cast can be readily acquired commercially (Koken Co. Ltd., Tokyo, Japan) (Pu et al. 2014, Pozzoli et al. 2016). The preserved cadaver head itself has also been used as a nasal cast, by implementing a multi-step process that plasticizes the cadaver heads through the displacement of liquids and lipids tissue components with a silicone polymer solution (Durand et al. 2011). More automated and contemporary strategies involve the use of patient MM scans to create 3D models that guide the rapid prototyping of full negative nasal cavity replicas (Zhou et al. 2013) or multi-component human nasal casts, partitioned either along the coronal axis or as major subregions of the nasal cavity (Xi et al. 2016, Shah et al. 2013, Foo et al. 2007, Cheng et al. 2001, Swift 1991). A series of corona MM images slices are replicated in up to 100 thin (≤2 mm thick) with micromilling in various polymer materials (Foo et al. 2007, Cheng et al. 2001, et al. Swift 1991). Other sectional casts are separated in to major vestibule, turbinate and olfactory nose regions, sometimes including throat portions, where individual parts are created with 3D printing methods (Xi et al. 2016, Shah et al. 2013).

While all the aforementioned nasal cast models can supply information on particle deposition within the upper airway, permit the analysis of the interaction of particles with the olfactory mucosal cells or tissue. Thus, they do not allow for the examination of absorption of inhaled particles or the histological examination of tissue subjected to varied types of conditioned air and inhalants. Several standard and non-conventional in-vitro techniques exist for performing nasal studies with consideration of cellular constituents of the nasal cavity. Standard in-vitro models involve culturing nasal epithelial cell lines at an air-liquid interface in a tranwell well system. In this set-up, cells are cultured atop a porous polymer membrane held in a support that separates a culture well into apical and basolateral compartments, respectively devoid and full of nutrient medium (Mercier et al. 2018). A handful of newly emergent chip-based systems were designed model an assortment of anatomical and functional features, associated with the nasal cavity (Na et al. 2017, Wang et al. 2014, Figueroa et al. 2010), including nasal glandular structures (Na et al. 2017), cilia beating patterns (Wang et al. 2014), and olfaction simulation with olfactory sensory neurons (Datta-Chaudhuri et al. 2016, Figueroa et al. 2010). 3D printing has also been implemented to modify a pharmaceutical tool that predicts the particle deposition from inhaled drug in the respiratory tract. The instrument traditionally comprises a cascade impactor attached to an induction chamber that respectively characterize particle deposition in the lower and upper respiratory tracts. A 3D printed version of the induction chamber contained chambers to fit transwell inserts holding ALI-conditioned nasal epithelial cells, and thus permitted the additional prediction of drug permeability and transport across the mucosal lining (Pozzoli et al. 2016). Nasal cast designs could benefit from the incorporation of regions that contain nasal cells or tissue.

Here we describe the construction of a 3D printed human nose simulator chamber, with anatomical accurate features and breathing functionality. The purpose of the nose simulator chamber is to observe and test different regions within a human nasal cavity replica and detect the physical effects of airborne particles within a human nose. The nose simulator chamber will consist of a base nasal chamber, segmented into equal coronal slices, which includes compartments for probing the airstream to measure air flow speed, particle distribution patterns, and particle-tissue interactions. A single sampling probe with interchangeable units used for introducing a flow sensor, TEM screens, and tissue layers within the walls of the interior nasal compartment.

Design and Construction of Nasal Simulator—Nose Simulator Face/nasopharynx Base: A collection of software was used to convert a CT scan-based stereolithography (STL) file to a face/nasopharynx base object, as well as create associated internal and external components.

The nasal cavity file was detected as "empty data" or multivariate data. This data acts as an image within the program and requires further processing to generate a file that could be edited in the construction of the nose simulator design. To convert "empty data" into recognizable data for 3D modeling programs, the nasal cavity file was imported into the Meshmixer program, a software tool developed to manipulate complex mesh features. Meshmixer was used to reduce the number of vertices and triangles, defining the nasal cavity design, from 100% to 25%, to optimize the surface for continuous design edits and changes, and exported as an STL file, compatible with Autodesk Inventor.

Using the MeshEnabler add-on application for Inventor, the nasal cavity was enhanced by converting all the mesh data from the negative nasal cavity region into a Solid Body part. The Solid Body Part format is a format where all the mesh data is identical within the .ipt file. This Solid Body Part is the optimal format for the additional further design implementation to 3D models rendered from and advancements on CT scan imaging. Using the MeshEnabler the .stl file of the nasal cavity was converted to an .ipt file to allow for editing. To create a 3D mold of the negative nasal cavity regions of the .ipt file, an extrusion of 77.64×101.96×85 mm was created as a separate solid body part to encase the nasal cavity and eventually form the negative. We utilized the combine and subtract tool on Using the newly formed extrusion and the nasal cavity as two solid bodies, the combine and subtract tool was used to turn two solid bodies into one body. By subtracting the cavity from the extrusion it created a negative of the cavity inside the extrusion.

Face/Nasopharynx Base Slides and Complementary Sampling Probes:

The face/nasopharynx base was sectioned into slices, using Autodesk Inventor. By integrating a series of planes equidistant from each other at 9.2 mm, the "Split" command was used to parse the extrusion into 9 separate slices. These nasal slices were then exported into an assembly for further editing.

Probing regions piercing the thickness of the coronal slices, creating channels from the left and right ends of the to the internal cavity features, were designed for all slices, except the first slide that presents external facial features, and the last slide that transitions into the pharynx region. Coronal sections of the nasal cavity CAD model were examined to identify probe sites at the superior, middle, and inferior meatus, the main passages or openings within the nasal cavity. These locations were selected to provide seamless integration with probes and result in minimal interference with the internal nasal structures and passages. There were a total of 25 total locations dispersed throughout the nasopharynx base created twelve (12) for one nostril and thirteen (13) on for the opposing nostril. A 6 mm-cylinder was cut through each cavity slide at a specified nasal site, resulting in a multi-piece cylinder, broken at open cavity regions, and the negative of the cylinder. The rod piece with ends containing nasal cavity contours at the site of interest (on either left or right cavity half) was saved as a separate file, while the negative of the cylinder and the cylindrical pieces in other regions were fused back together. The two resulting objects were saved as individual files for further manipulation. The diameter of the contoured rods were shaved down to 5.6 mm to ensure proper tolerances for ease of fitting following printing. A teeth and groove lock was created to fix each probe into its corresponding slide. This was achieved by adding two staggered teeth to the rod piece, 10 mm from the contoured tip, and extruding complemental L-shaped groove paths into the slide. An end piece with an alphanumeric label and finger grip was combined with the probe body probe identification and handling. The end piece had a slightly larger diameter (7.6 mm), and a complemental hole was extruded from the slice to fit the piece, and the end unit facilitates formation of an airtight lock upon sealing.

To ensure an airtight seal upon stacking all slides, a gasket was incorporated on the front face of each slide, and threaded openings were bored through each slide on each corner to permit tightening screws. There are three variations (A, B-F, G and end slice variations) of gaskets that are equidistant to their opposing side 2 mm in width. Each gasket ring is integrated into a recessed border region of the slide. The gasket has a total thickness of 0.75 mm, with 0.50 mm embedded and 0.25 mm protruding, and width of 0.5 mm; these dimensions allow an optimal level of gasket expansion upon compression.

Cylindrical inserts were designed to fit into each probing site. There were three insert variations: (1) a resting insert to fill the opening of a region not being tested, (2) an anemometer insert, to fit a flow meter probe and sample air flow velocity, and (3) a tissue insert, to examine the effects of various inhaled airstreams on tissue. All inserts included and custom contouring of ends to align with the internal anatomical geometry of the nasal cavity. The cylindrical anemometer probe was custom designed to hold the omnidirectional velocity probe (mini I shape, V, Kanomax, 6551-2G) of a research grade handheld hot-wire anemometer (Kanomax, 6501-CE). The multi-part anemometer rod contained a channel path for the anemometer probe unit and attached cord and inset to ensure an airtight seal. For the tissue insert probes, a centered circle was extruded from the center of the rod tip to create a cylindrical recession for housing tissue-like constructs. The plane of extrusion plane was set as the lowest geometric polygon on the rod tip and existing within the 4.5 mm diameter circle.

Slides and probe rods were printed with a Stratasys Objet500 polyjet 3D printer, using multiple materials: rigid transparent acrylic (VeroClear, Stratasys) for bulk regions of the nasal slides and probes and a semitransparent rubber-like material (Agilus30, Stratasy) for slide gaskets.

Sliding base system: A sliding base system was created to hold and allow bidirectional translocation along the base for easy slide manipulation and access to desired cavity regions. A plastic track was designed with a groove that slid over the ridge at the bottom of a single slide, while being closed at one end to lock the slide in place. All the slide-track units were inserted into the grooved aluminum rails (8020.net, 25-5013-Black-FB), after which the slides could be compressed together and locked in place with the screws. A transitional structure was designed to be integrated into the base system to connect the pharynx of the last slide to the opening of the custom fan. The tracks and transition structure were designed using Autodesk Inventor and produced with a Carbon Digital Light Synthesis 3D printer, using a rigid polyurethane material (Carbon, RPU70).

A centrifugal-like fan was created to generate bi-directional airflow within the nasal cavity. An .stl file of the fan assembly was designed with 3D CAD software (Autodesk Inventor) and printed with rigid polyurethane (RPU, Carbon 3D) material on a digital light synthesis (DLS) 3D printer. The body of the fan is comprised of a cylindrical outer casing with two channels that function as relative inlets and outlets for airflow. These channels are separated by 90° and reside within the same plane. The cross-sectional area of both channels is 10 mm×18 mm, which is comparable to that of the model's nasopharynx. A 5-blade fan (blade length=34 mm) rests on a central axis within the housing. The fan rotation is driven by a 12V DC motor, positioned next to the fan axis outside the enclosed casing. A custom-built acrylic box was designed to house the fan and electronic hardware.

Fan Integration for Airflow Generation: An Arduino Uno microcontroller was used to regulate the amount of voltage and direction of electrical current flow supplied to the motor, which are respectively proportional to the airflow rate and direction. Voltage applied to the motor can be set between 0-12V, and is proportionally scaled to the Arduino's pulse width modulation (PWM) output of 0-5V. This effect was achieved through use of a voltage regulator circuit, where the Vin source of 12V was adjusted to the desired voltage. To simulate both inhalation and exhalation, the current flowing through the motor was reversed through a single-pull double-relay circuit.

An on-computer GUI, created in Matlab's App Designer Software, is used to operate the fan unit in the nose simulator. The user is able to select the desired inhalation and exhalation waveforms and edit their various parameters (i.e. amplitude, breath duration, resting period, etc.). Additional features to compensate for consistency in total lung capacity (TLC) and back electromagnetic flux (BEMF) of the motor are incorporated into the GUI generated waveforms as well.

Breathing Simulation: A graphical user interface (GUI) for interacting with fan flow rate and direction was programmed with Matlab's App Designer. This GUI application was downloaded and installed on a computer, independent of a Matlab license requirement. The application shares information directly to the simulator device via a USB serial connection.

Figure 2:
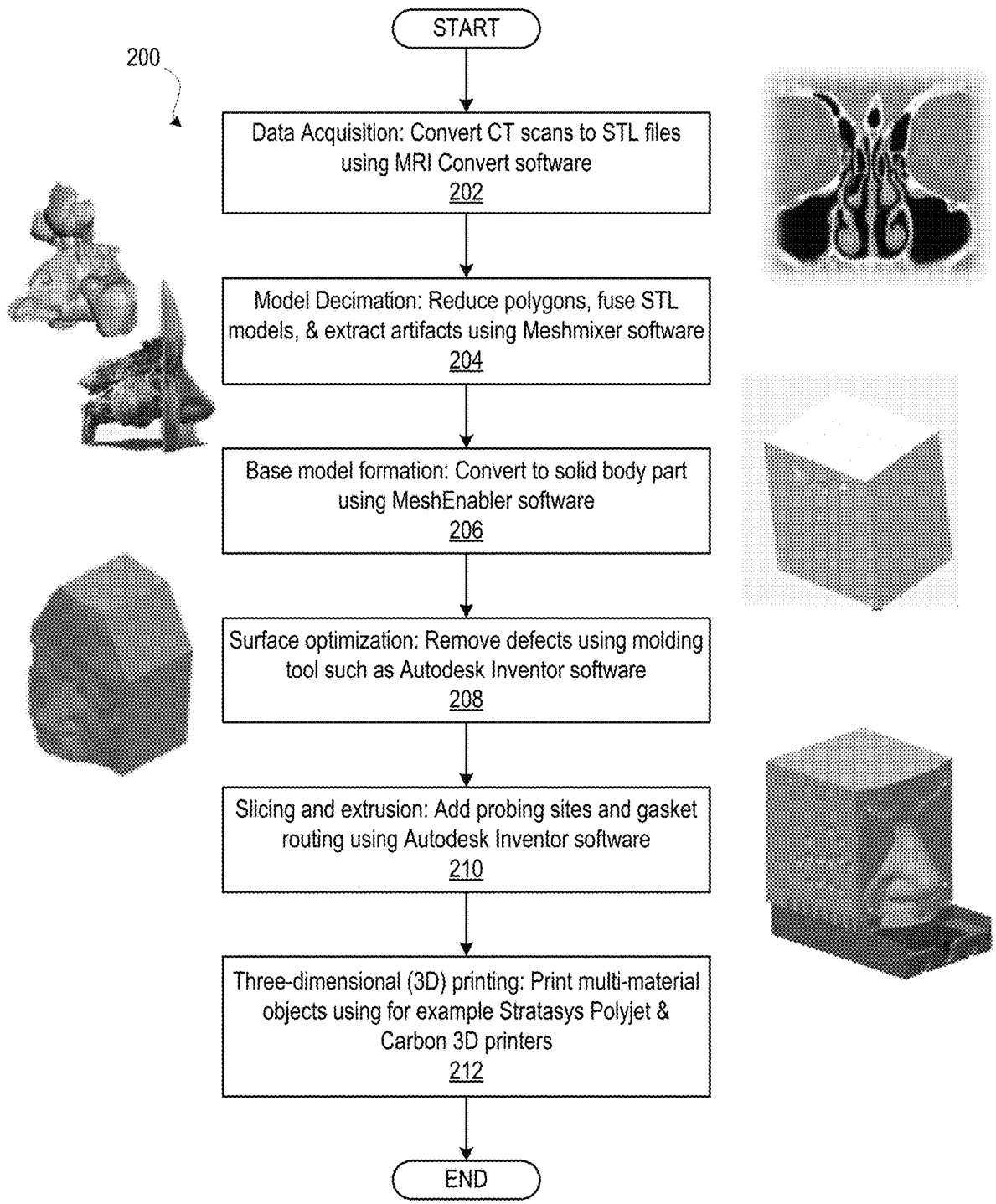
FIG. 2 depicts a flow diagram of a method used to create the 3D printed breathing human nose simulator of FIG. 1, according to one or more embodiments.

RESULTS AND DISCUSSION: In summary, FIG. 2 depicts a flow diagram of a method 200 used to create the 3D printed breathing human nose simulator 100 (FIG. 1). Method 200 includes Data Acquisition: converting CT scans to STL files using Mill Convert software (block 202). Method 200 includes Model Decimation: reducing polygons, fuse STL models, & extract artifacts using Meshmixer software (block 204). Method 200 includes Base model formation: converting to solid body part using MeshEnabler software (block 206). Method 200 includes Surface optimization: removing defects using molding tool such as Autodesk Inventor software (block 208). Method 200 includes Slicing and extrusion: adding probing sites and gasket routing using Autodesk Inventor software (block 210). Method 200 includes Three-dimensional (3D) printing: printing multi-material objects using for example Stratasys Polyjet & Carbon 3D printers (block 212). Then method 200 ends.

Using a collection of CAD software, 3D printers, machining tools, assorted materials and Arduino electronic platforms, we successfully designed a nose simulator system featuring: anatomically-precise human nasal cavity regions, a custom-built fan system to mimic human cyclic and noncyclic breathing patterns, and compartments to probe airstream for flow velocity, tissue-inhalant interaction, and particulate distribution.

We used multi-material 3D printing to produce a nasopharynx cast complete with vestibular, inferior turbinate, medial turbinate, superior turbinate, and nasopharynx regions internally, and nose and facial feature externally. A collection of software was used to convert computed tomography (CT) scan-based stereolithography (STL) file to create a face/nasopharynx base object, as well as the associated internal and external components.

Figure 3A:
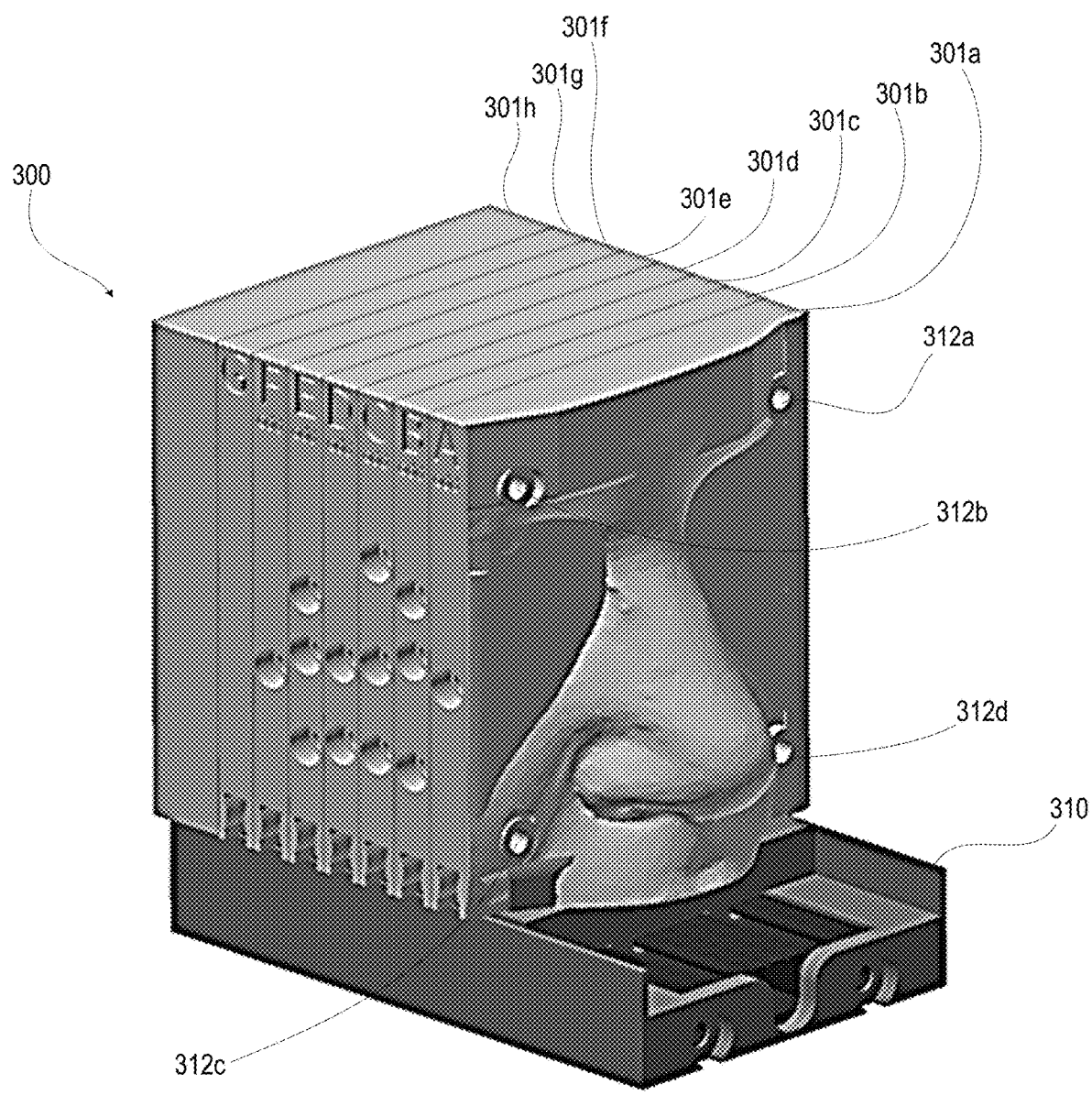
FIG. 3A is a 3D view of the construction of the nasopharynx base object, according to one or more embodiments.
Figure 3B:
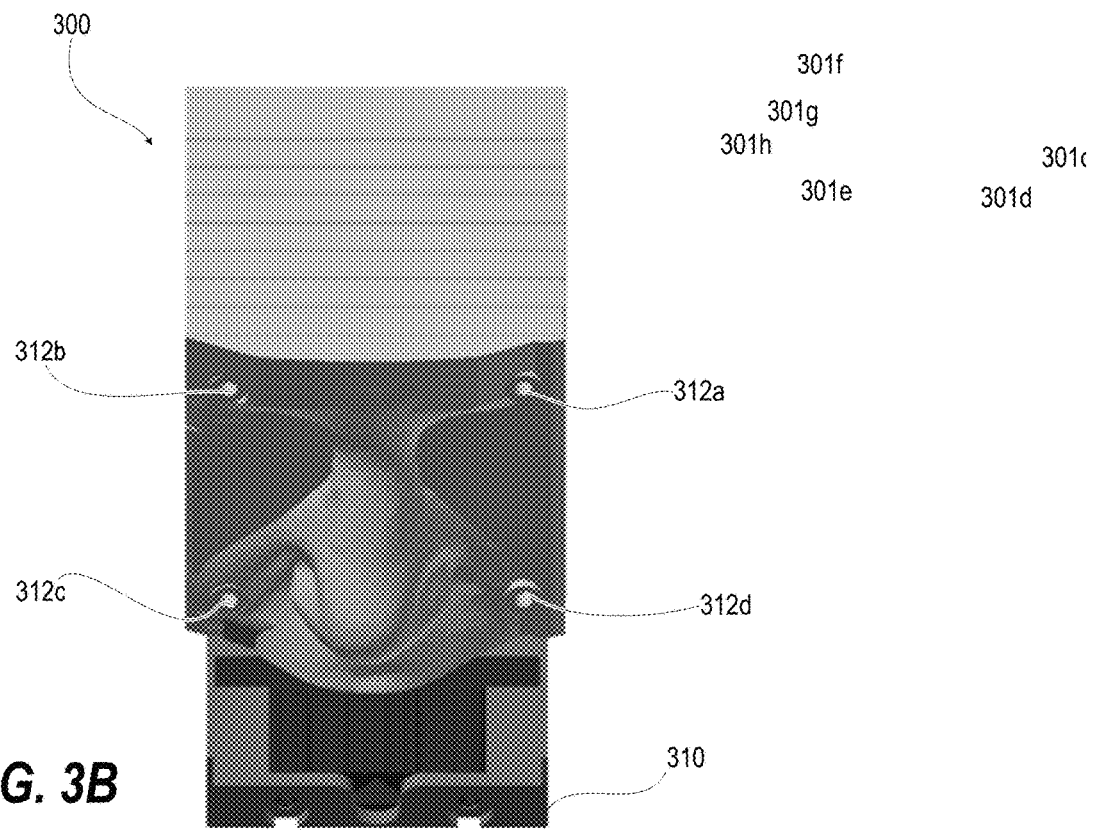
FIG. 3B is a top front view of the nasopharynx base object of FIG. 3A, according to one or more embodiments.
Figure 3C:
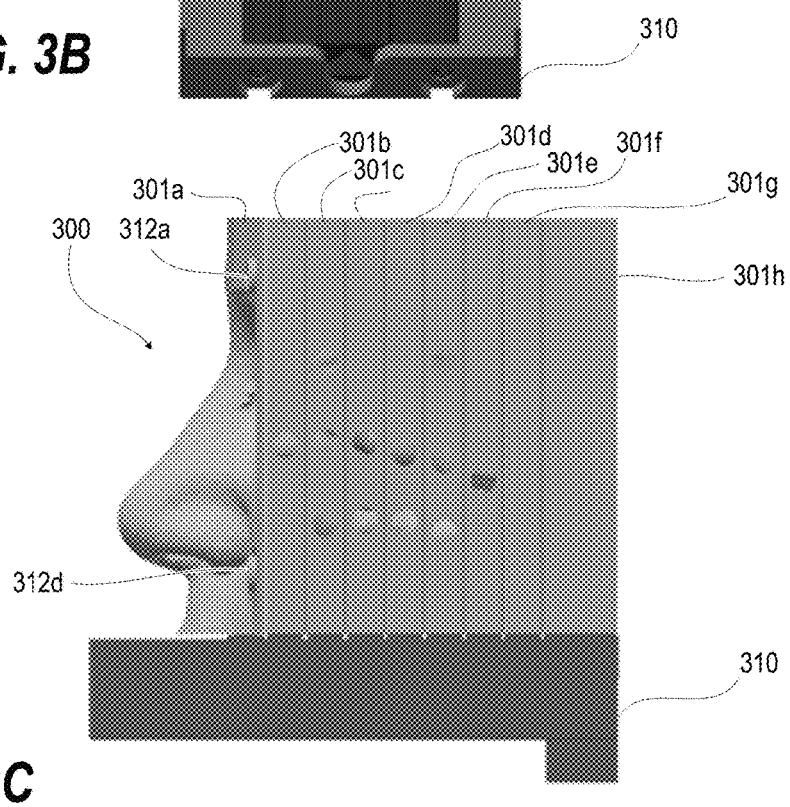
FIG. 3C is a left view of the nasopharynx base object of FIG. 3A, according to one or more embodiments.
Figure 4A:
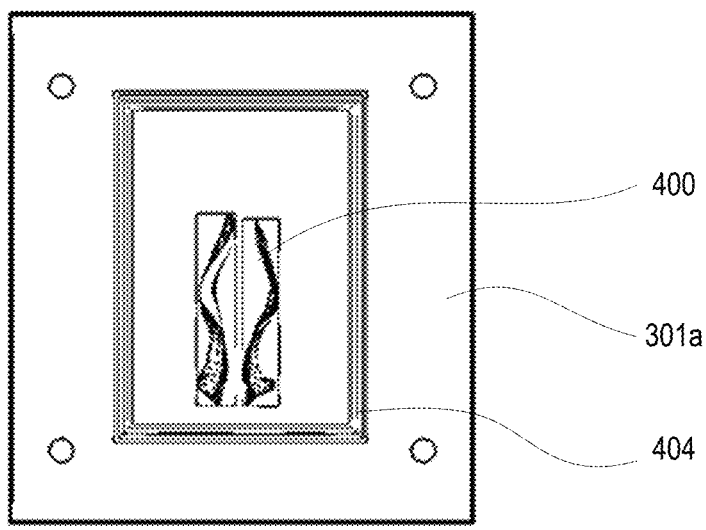
FIG. 4A is a front view of a portion of 3D printed nasal cavity contained in a first slide, according to one or more embodiments.
Figure 4B:
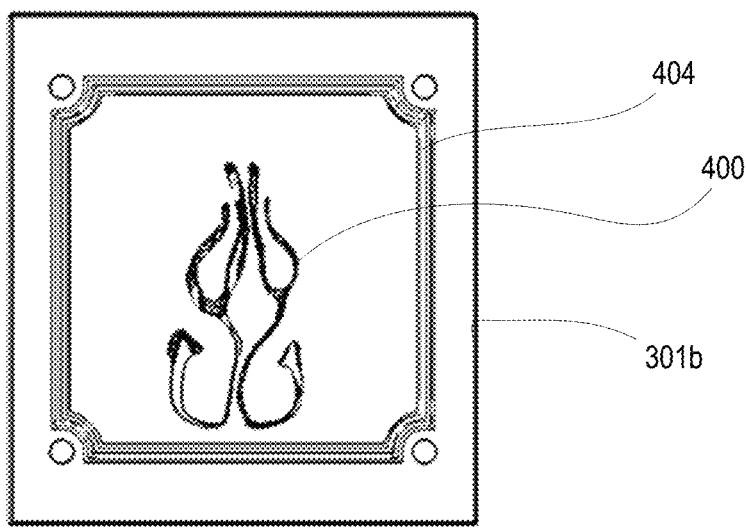
FIG. 4B is a front view of a portion of 3D printed nasal cavity contained in a second slide, according to one or more embodiments.
Figure 4C:
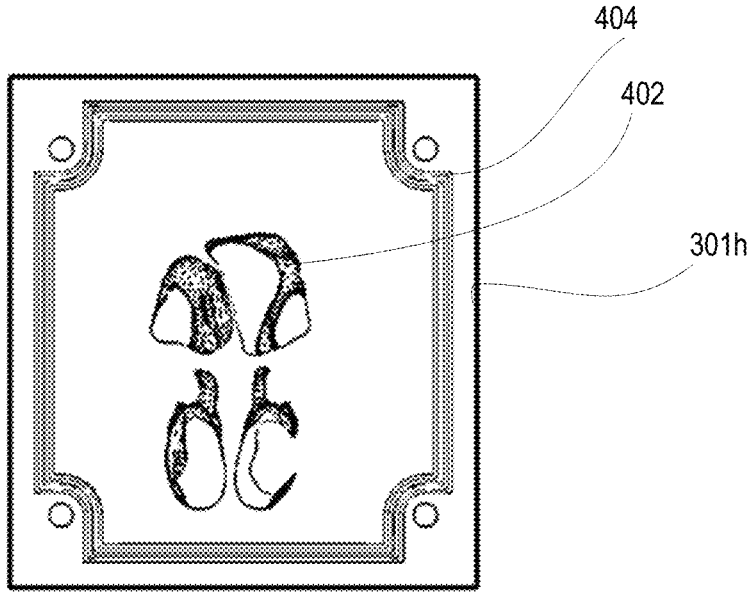
FIG. 4C is a front view of a portion of a 3D printed pharynx of the 3D printed nasal cavity contained in a last slide, according to one or more embodiments.

FIG. 3A is a 3D view of the construction of the nasopharynx base object 300. FIG. 3B is a top front view of the nasopharynx base object 300 of FIG. 3A. FIG. 3C is a left view of the nasopharynx base object 300 of FIG. 3A. FIG. 4A is a front view of a portion of 3D printed nasal cavity 400 contained in slide 301a. FIG. 4B is a front view of a portion of 3D printed nasal cavity 400 contained in slide 301*b*, which is representative of other non-end slides 301*c*-301*g* (FIGS. 3A-3C). FIG. 4C is a front view of a portion of a 3D printed pharynx 402 of the 3D printed nasal cavity 400 contained in slide 301*h*.

With primary reference to FIGS. 3A-3C, the nasopharynx base object 300 was sectioned into eight (8) slides. The nasopharynx base object 300 was sectioned into eight (8) slides 301*a*-301*g*, one (1) section 301*a* containing the external facial features, 6-mm sections spanning the 3D printed nasal cavity 400 (FIGS. 4A-4C), and one 12-mm slide 301*h* integrating a 3D printed pharynx 402 (FIG. 4C). The slides 301*a*-301*g* were aligned on an aluminum railing 310 to allow easy manipulation of slides 301*a*-301*h*. Four partially threaded screws 312*a*-312*d* piercing each slice 301*a*-301*h* allow for compression when tightened. With reference to FIGS. 4A-4C, respective rubber-like gasket 404 was fused onto the front of each slice 301*b*-301*h* to allow airtight seal of entire nasopharynx base object 300 (FIGS. 3A-3C).

Figure 5A:
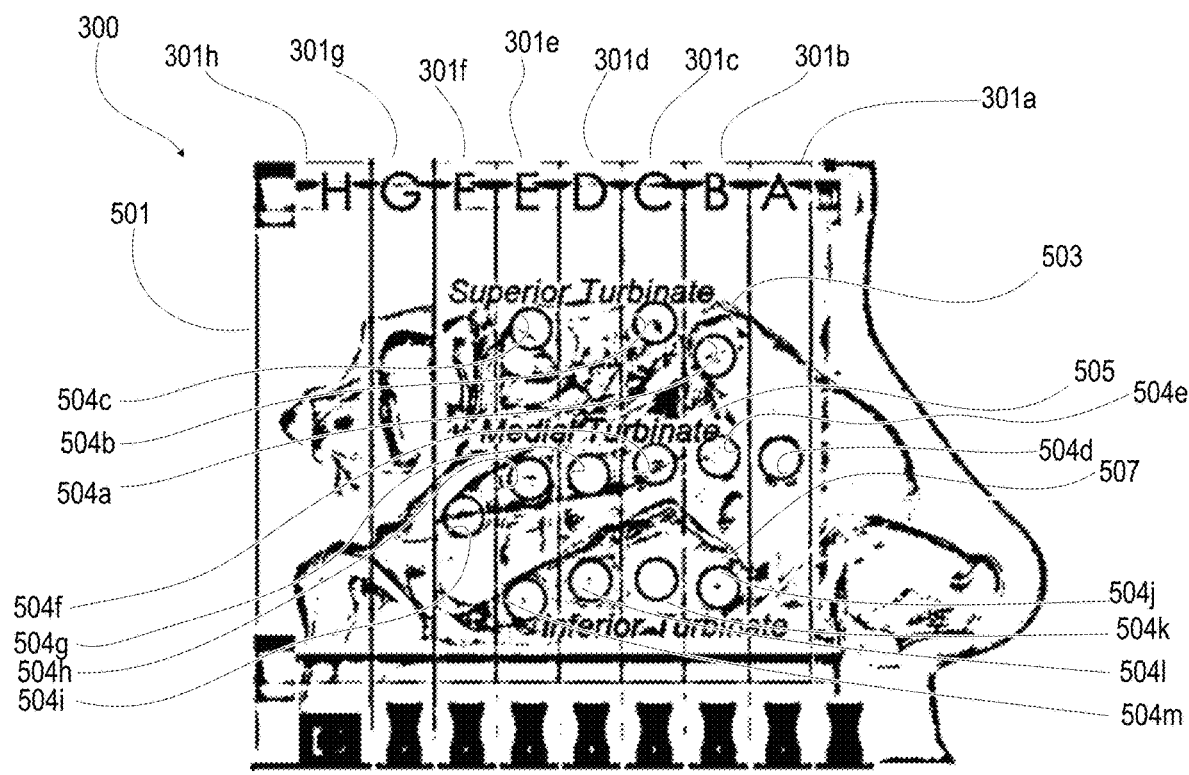
FIG. 5A depicts a right side view of the nasopharynx base object, according to one or more embodiments.
Figure 5B:
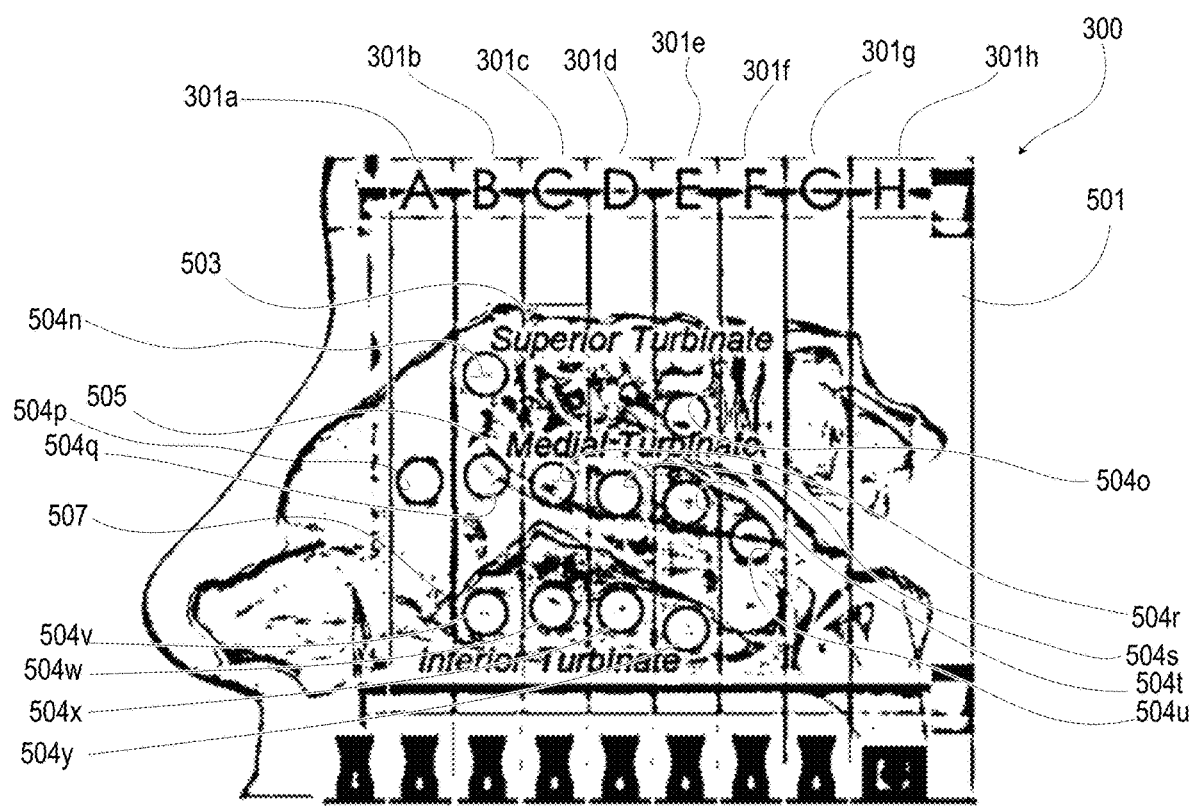
FIG. 5B depicts a left side view of the nasopharynx base object, according to one or more embodiments.

FIGS. 5A-5B respectively depict a right side view and a left side view of the nasopharynx base object 300. Probing regions or channels were inserted into the thickness of the slides 301*a*-301*f*. Specific sites for sampling at the superior, middle, and inferior meatus, the main passages or openings within the nasal cavity 400 were identified through examination of the CAD model. These locations were selected to provide seamless integration with probes and result in minimal interference with the internal nasal structures and passages. With reference to FIG. 5A, a chamber 501 of nasopharynx base object 300 is depicted transparently to expose superior turbinate 503 of 3D printed nasal cavity 400 accessible from the right via probe access bores 504*a*-504*c* respectively in slides 301*b*, 301*c* and 301*e*. Medial turbinate 505 of 3D printed nasal cavity 400 is accessible from the right via probe access bores 504*d*-504*i* respectively in slides 301*a*-301*f*. Inferior turbinate 507 of 3D printed nasal cavity 400 is accessible from the right via probe access bores 504*k*-504*m* respectively in slides 301*b*-301*e*. With reference to FIG. 5B, the superior turbinate 503 is accessible from the left via probe access bores 504*n*-504*o* respectively in slides 301*c* and 301*e*. Medial turbinate 505 is accessible from the left via probe access bores 504*p*-504*u* respectively in slides 301*a*-301*f*. Inferior turbinate 507 of 3D printed nasal cavity 400 is accessible from the left via probe access bores 504*v*-504*y* respectively in slides 301*b*-301*e*.

Figure 6A:
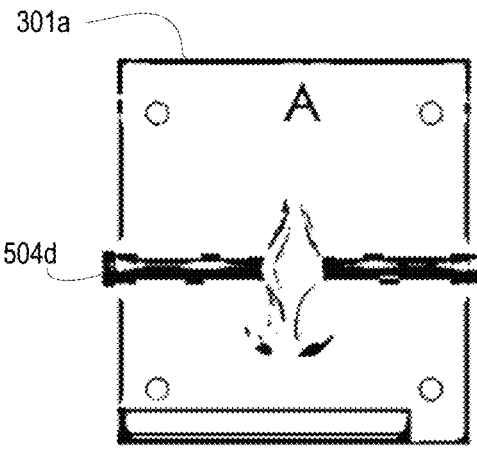
FIG. 6A depicts a front view of a first slide having one right probe access bore and one left probe access bore, according to one or more embodiments.
Figure 6B:
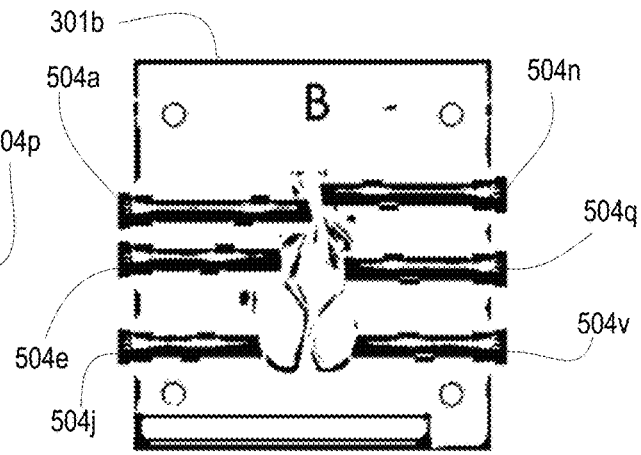
FIG. 6B depicts a front view of second slide having three right probe access bores and three left probe access bores, according to one or more embodiments.
Figure 6C:
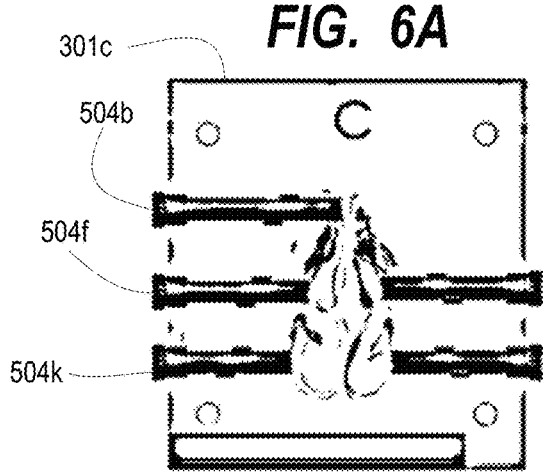
FIG. 6C depicts a front view of a third slide having three right probe access bores and two left probe access bores, according to one or more embodiments.
Figure 6D:
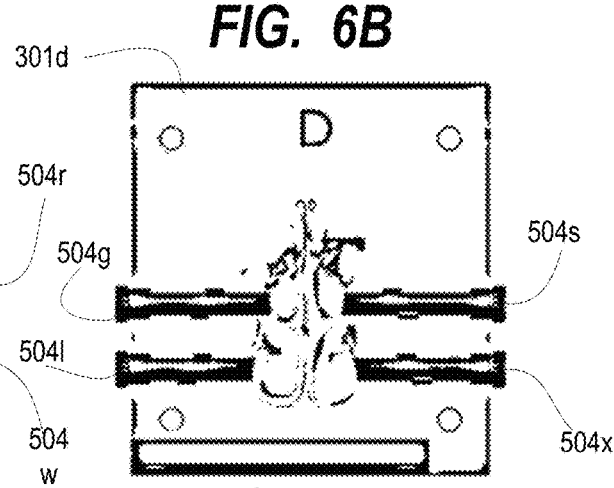
FIG. 6D depicts a front view of fourth slide having two right probe access bores and two left probe access bores, according to one or more embodiments.
Figure 6E:
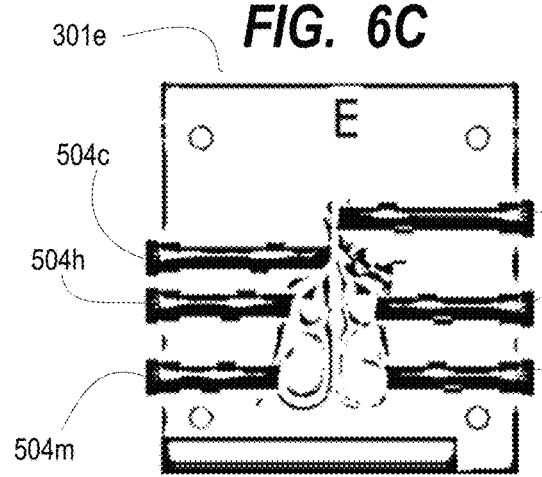
FIG. 6E depicts a front view of fifth slide having three right probe access bores and three left probe access bores, according to one or more embodiments.
Figure 6F:
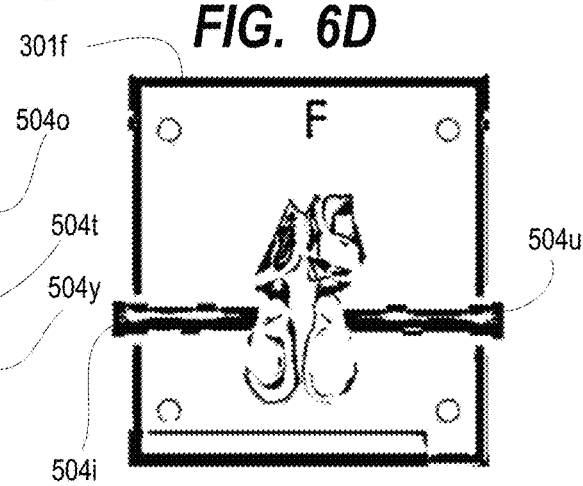
FIG. 6F depicts a front view of sixth slide having one right probe access bore and one left probe access bore, according to one or more embodiments.

FIG. 6A depicts a front view of slide 301*a* having one right probe access bore 304*d* and one left probe access bore 304*p*. FIG. 6B depicts a front view of slide 301*b* having three right probe access bores 304*a*, 304*e*, and 304*j* and three left probe access bores 304*n*, 304*q*, and 304*v*. FIG. 6C depicts a front view of slide 301*c* having three right probe access bores 304*b*, 304*f*, and 304*k* and two left probe access bores 304*r* and 304*w*. FIG. 6D depicts a front view of slide 301*d* having two right probe access bores 304*g* and 304*l* and two left probe access bores 304*s* and 304*x*. FIG. 6E depicts a front view of slide 301*e* having three right probe access bores 304*c*, 304*h*, and 304*m* and three left probe access bores 304*o*, 304*t*, and 304*y*. FIG. 6F depicts a front view of slide 301*f* having one right probe access bore 304*i* and one left probe access bore 304*u*.

FIG. 7A depicts a side view of a cylindrical rod 701*a* of a particular length corresponding to a probe access bore and having a perpendicular distal face 703*a* that aligns with a perpendicular contour at a location of a 3D printed nasal cavity 705. FIG. 7B depicts a side view of a cylindrical rod 701*b* of a shorter particular length corresponding to a shorter probe access bore and having a non-perpendicular distal face 703*b* that aligns with a non-perpendicular contour at a location of the 3D printed nasal cavity 705. Cylindrical rod 701*a* (FIG. 7*a*), 701*b* are resting inserts that seal process access bores that are not accessed.

FIG. 7C depicts an anemometer 710 being inserted through an anemometer insert 711*a* that was custom design to fit a commercial miniature spherical probe of a flow meter (omni-directional velocity probe, mini I shape, V, Kanomax, 6551-2G), permitting sampling of air flow velocity. The anemometer insert 711*a* has a perpendicular distal face 713*a*. FIG. 7D depicts the anemometer 710 inserted through the anemometer insert 711*a*. FIG. 7E depicts the anemometer 710 inserted through an anemometer insert 711*b* that has a non-perpendicular distal face 713*a*.

FIG. 7F depicts a tissue insert 720 having a cylindrical shaft 721 of a length selected to position a tissue holder 722. The tissue holder 722 has distal disc recession 724 sized to receive a gel medium 726 and a living tissue sample 728. In One or embodiments, the disc recession 724 has a diameter of 4.5 mm and a thickness of 1.5 mm that can hold a gel medium 726 covered with a living tissue sample 724 of circular nasal tissue explants or cutouts of stacked nasal epithelial cell layers. To minimally interfere with the intricate internal nasal cavity architecture, all inserts were designed with custom contoured of ends that matched internal anatomical geometry of the nasal cavity.

Figure 8A:
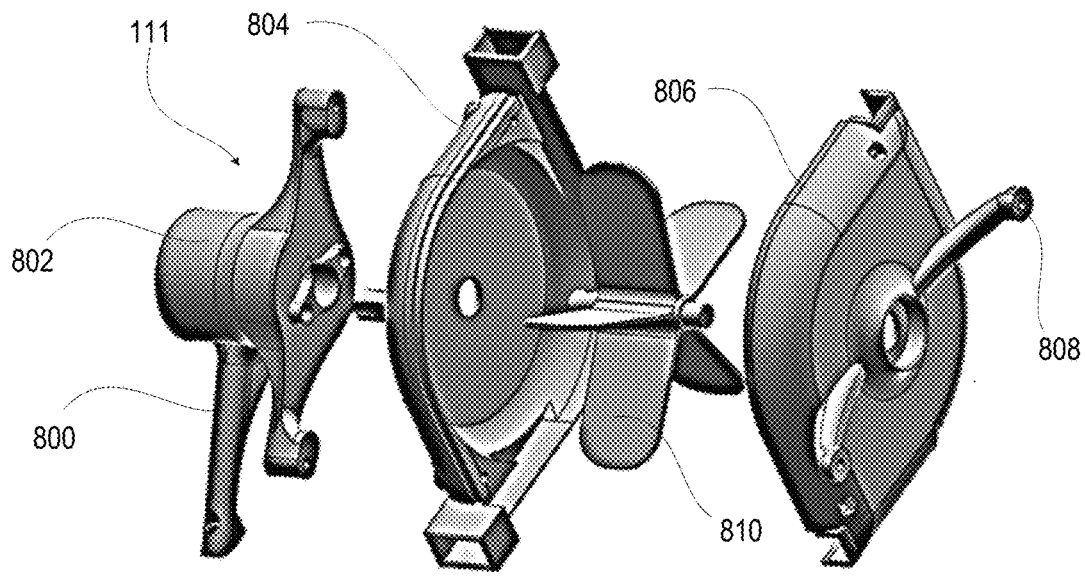
FIG. 8A is an exploded 3D view of the bi-directional fan that includes a stand that includes a motor encasing that mounts to back cover that in turn attaches to a front cover having a mount, according to one or more embodiments.
Figure 8B:
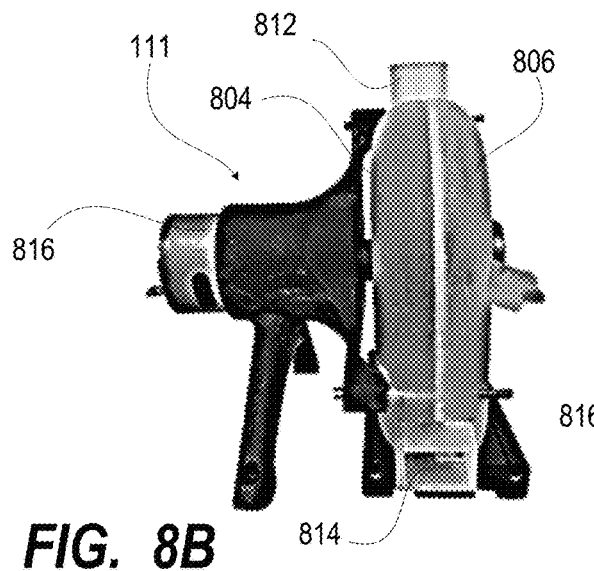
FIG. 8B is a side view of the bi-directional fan depicting assembled back and front covers to form a top air port and a bottom air port, according to one or more embodiments.
Figure 8C:
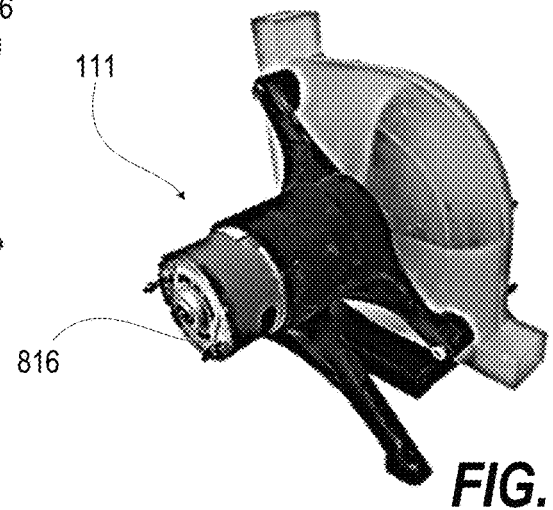
FIG. 8C is a back view of the bi-directional fan depicting a motor that includes motor set-screw and ball bearing to stabilize fan blade spin, according to one or more embodiments.
Figure 8D:
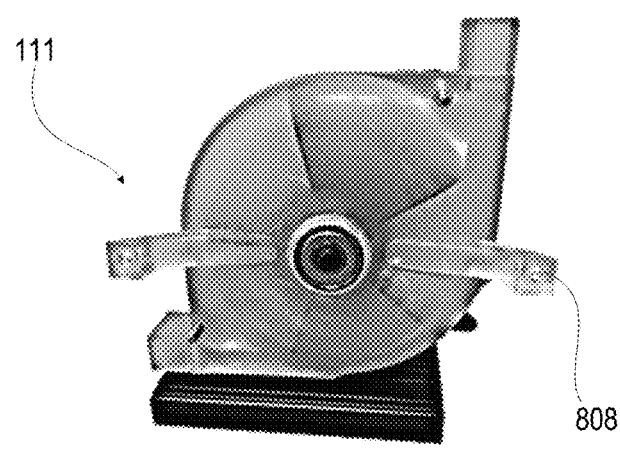
FIG. 8D is a front view of the bi-directional fan depicting the mount that is attachable to a side wall of the fan container of FIG. 1, according to one or more embodiments.

FIG. 8A is an exploded 3D view of the bi-directional fan 111 that includes a stand 800 that includes a motor encasing 802 that mounts to back cover 804 that in turn attaches to a front cover 806 having a mount 808. The back and front covers 804, 806 encompass a fan blade 810. FIG. 8B is a side view of the bi-directional fan 111 depicting assembled back and front covers 804, 806 to form a top air port 812 and a bottom air port 814. The top and bottom air ports 812, 814 operate either as an air inlet or air outlet depending on the direction of spin of the fan blade 810. FIG. 8C is a back view of the bi-directional fan 111 depicting a motor 816 that includes motor set-screw and ball bearing to stabilize fan blade spin. FIG. 8D is a front view of the bi-directional fan 111 depicting the mount 808 that is attachable to a side wall of the fan container 112 (FIG. 1).

Figure 9A:
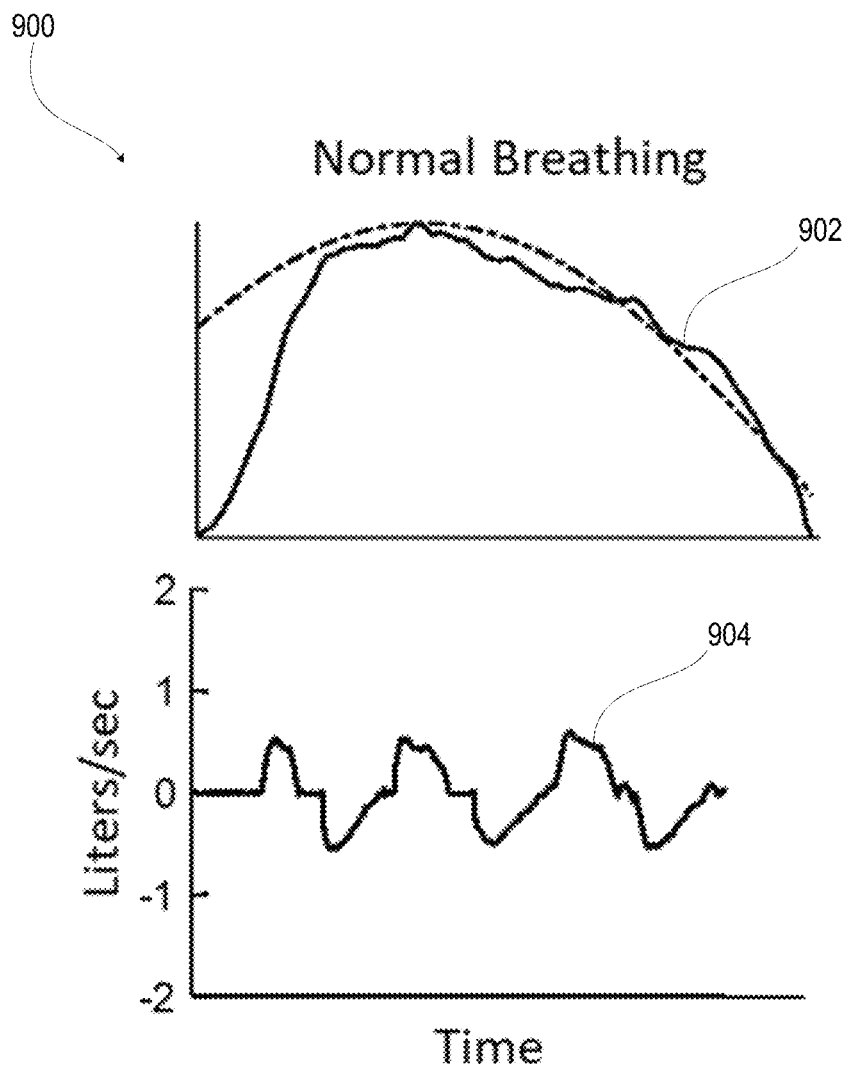
FIG. 9A depicts a graphical plot of a normal breathing pattern inhalation/exhalation airflow patterns, according to one or more embodiments.
Figure 9B:
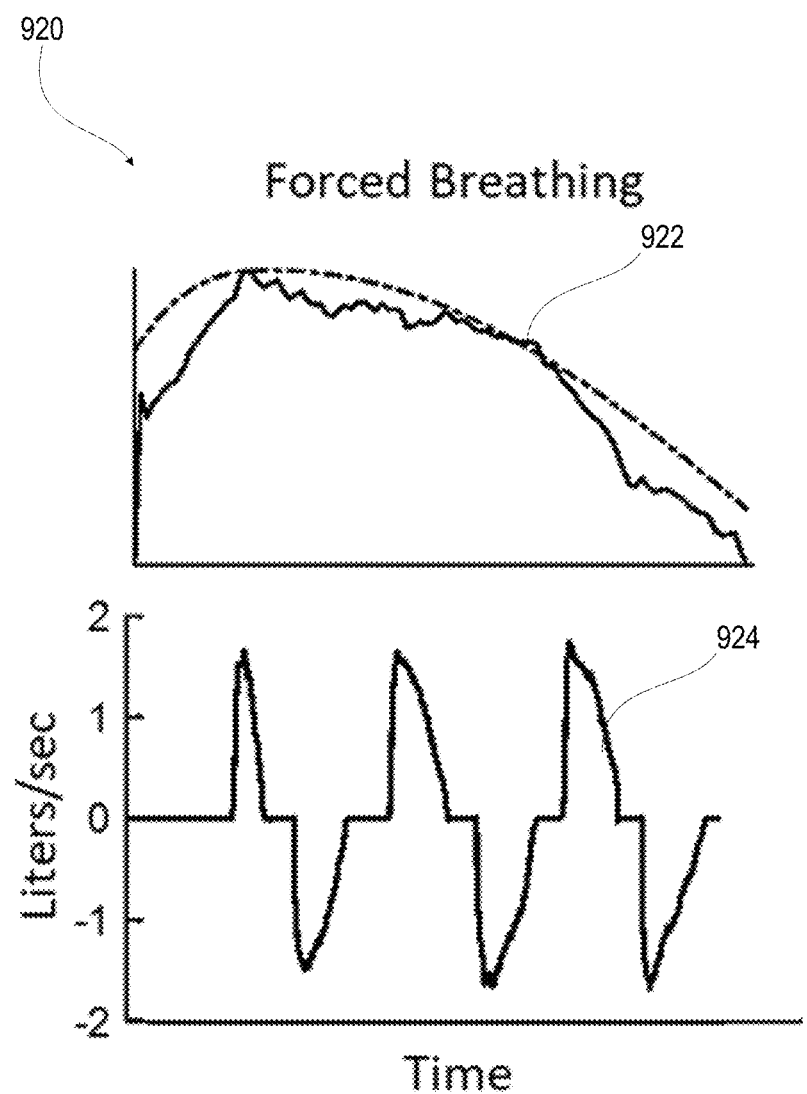
FIG. 9B depicts a graphical plot a forced breathing pattern inhalation/exhalation airflow patterns, according to one or more embodiments.

The bi-directional fan 111 (FIGS. 8A-8D) simulates inhalation and exhalation rates. In one or more embodiments, motor voltage and current flow direction are regulated via Arduino Uno microcontroller, while breathing pattern waveform, rate, duration, etc. are all executed via a graphical user interface (GUI). FIG. 9A depicts a normal breathing inhalation/exhalation airflow patterns 900. In particular, an upper plot 902 presents volume of air moved as a function of time and a lower plot 904 presents a rate of change in volume as a function of time. FIG. 9B depicts a forced breathing inhalation/exhalation airflow patterns 920. In particular, an upper plot 922 presents volume of air moved as a function of time and a lower plot 924 presents a rate of change in volume as a function of time.

Figure 10:
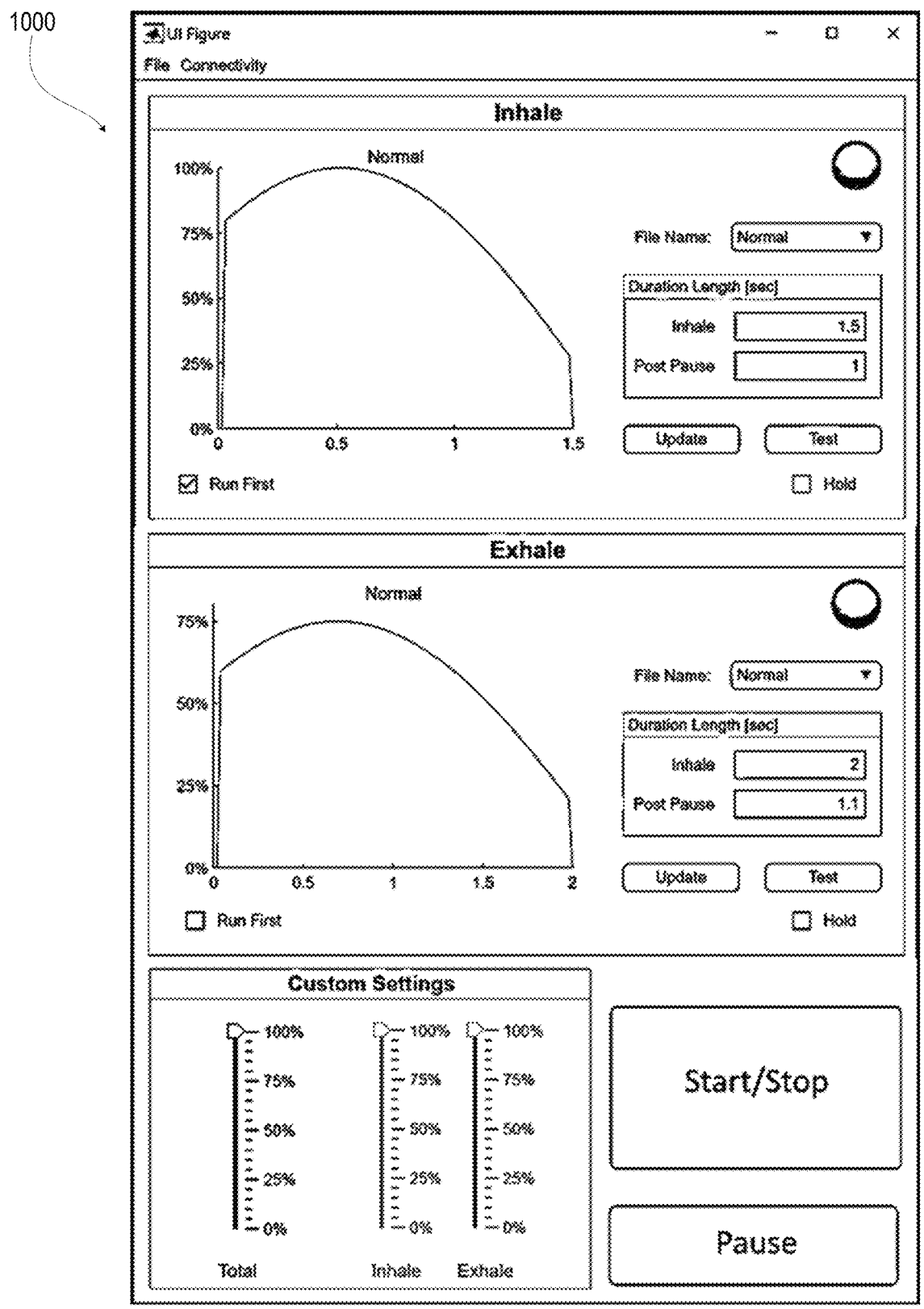
FIG. 10 depicts a screen shot of a Matlab graphical user interface (GUI) used to control flow modes and sequence, according to one or more embodiments.

FIG. 10 is a screen shot 1000 of a Matlab graphical user interface (GUI) used to control flow modes and sequence. The application shares information directly to the simulator device via a USB serial connection. Upon opening the application, connection to the Arduino is established by specifying the appropriate communication port (COM port). From this point, the fan is fully controllable with a wide selection of cyclic and non-cyclic functions. The user is able to select the waveform shape and the inhale and exhale flow rate amplitude, which directly correlates to the voltage received by the fan.

Unlike typical nasal cast models, this innovative biohybrid upper respiratory model allows for more accurate representation of physiological breathing functions coupled with spatiotemporally relevant tissue analysis. However, like general nasal cast models, there are several future modifications that can be added to the design to supply a breathing systems closer to the bonifide nose. First, the nasal cavity region is fixed and rigid (Doody et al 2008). Therefore, preset forms of nasal casts are unable to mimic the natural cyclic alternation in open and closed caliber and high and low airflow of the nostrils (Eccles 2000, Beule 20110). It is possible to replicate the nasal cycling using flexible materials and including mechanical structures to facilitate expansion and contraction of a nostril opening. Second the printable materials do not exhibit the stiffness of hard and soft regions of the human nose. Sander et al. created a nasal cast, for patient education, with rigid and flexible materials to represent the hard and soft tissues existing within the nasal cavity (Sander et al 2017). We have used the same materials for the existing design, but the rigid materials was used for the bulk nasal cavity design and the flexible materials to facilitate an airtight seal between individual slides. With an ever increasing production of diverse printable materials, possessing a range of mechanical properties, it is possible to create a nasal simulator containing regions that match the hard and soft tissue moduli of a bonifide nasal cavity.

The nasal cavity geometry should be carefully determined, based on research needs. Some researchers have determined geometries of a "standard" nasal cavity by averaging the geometries from 3D cavity models derived from 30 patients (Liu et al 2009). Also, with 3D printing, it is possible to create group or patient-specific replicas to account for possible variations in research results due to factors such as age, race, sex or existing nasal anomalies (e.g. presence of nasal polyps).

CONCLUSIONS: A 3D printed model of nose simulator chamber was designed and created using rapid prototyping, machining and programming methods. The technique utilized 3D mesh and modeling software along with rapid innovation 3D printers to generate single material structures The protocol reported here focuses on converting Nasal Cavity CT data into the 3D printed design for testing. 3D printing of nose simulator chamber is a prodigious design for testing of patterned distribution and flow patterns of inhaled airstreams within the nasal cavity, and the interaction of inhalants with nasal mucosa cells or tissue.

Ongoing work will include validation of this nose simulator system by characterizing the achievable flow rates within the nose simulator device (using the commercial anemometer tip). Additionally, we will integrate nasal tissue or tissue-like (multi-cell layers) into the "tissue" probes and characterize the variation of cellular viability with time.

Prospective experiments include the evaluation of different potentially hazardous environmental conditions, including hypoxia, airborne nanoparticles, and exposure to volatile organic compounds. Here we have married electronic and biological elements in a proposal to develop a robotic biohybrid upper respiratory model. In doing so, we strive to raise the achievement bar for bioengineering technologies a bit higher by pushing the development of more life-like robotic devices that doubly supply advanced mechanical function and biological architecture that are native to humans.

Additional information is provided in the following references, the disclosure of which is hereby incorporated by reference in their entirety:

Beule, Achim G. "Physiology and pathophysiology of respiratory mucosa of the nose and the paranasal sinuses." *GMS current topics in otorhinolaryngology, head and neck surgery* 9 (2010).

Bondy, S. C. (n.d.). Neurotoxicity of Nanoparticles. In S. C. Sahu & D. A. Casciano (Eds.) (2014). *Handbook of Nanotoxicology, Nanomedicine and Stem Cell Use in Toxicology*. Chichester, West Sussex, United Kingdom: Wiley. (pp. 111-119).

Cheng, Y. S., Holmes, T. D., Gao, J., Guilmette, R. A., Li, S., Surakitbanharn, Y., & Rowlings, C. (2001). Characterization of nasal spray pumps and deposition pattern in a replica of the human nasal airway. Journal of Aerosol Medicine, 14(2), 267-280.

Chun, S. I., & Mun, C. W. (2015). Cytotoxicity of TSP in 3D agarose gel cultured cell. *PloS one,* 10(6).

Ding, C., Yi, X., Jiang, C., Xu, H., Yan, X., Zhang, Y. Lin, H. (2019). Development and validation of a multi-color model using 3-dimensional printing technology for endoscopic endonasal surgical training. *American Journal of Translational Research,* 11(2), 1040-1048.

Dong, J., Shang, Y., Inthavong, K., Chan, H., & Tu, J. (2018). Partitioning of dispersed nanoparticles in a realistic nasal passage for targeted drug delivery. *International Journal of Pharmaceutics,* 543(1-2), 83-95.

Doorly, D., Taylor, D., Gambaruto, A., Schroter, R., & Tolley, N. (2008). Nasal architecture: Form and flow. Philosophical Transactions of the Royal Society A: Mathematical, *Physical and Engineering Sciences,* 366(1879), 3225-3246.

Durand, Marc, Jérémie Pourchez, Bruno Louis, Jean-Francois Pouget, Daniel Isabey, André Coste, Jean-Michel Prades, Philippe Rusch, and Michele Cottier. "Plastinated nasal model: a new concept of anatomically realistic cast." (2011).

Eccles, R. (2000). Nasal airflow in health and disease. Acta oto-laryngologica, 120(5), 580-595.

Evans B. 2012. Action hero mashups. In: Evans B (Editor). Practical 3D Printers: The Science and Art of 3D Printing. 1st Ed. New York, N.Y.: Springer Science 1 Business Media. p 163-193.

Datta-Chaudhuri, Timir, et al. "Olfaction on a chip." *Sensors and Actuators B: Chemical* 235 (2016): 74-78.

Figueroa, Xavier A., et al. "Large-scale investigation of the olfactory receptor space using a microfluidic microwell array." Lab on a Chip 10.9 (2010): 1120-1127.

Foo, M. Y., Cheng, Y. S., Su, W. C., & Donovan, M. D. (2007). The influence of spray properties on intranasal deposition. *Journal of Aerosol Medicine,* 20(4), 495-508.

Giannatsis J, Dedoussis V. 2009. Additive fabrication technologies applied to medicine and health care: A review. Int J Adv Manuf Tech 40:116-127.

Hallworth, G. W., & Padfield, J. M. (1986). A comparison of the regional deposition in a model nose of a drug discharged from metered aerosol and metered-pump nasal delivery systems. *Journal of allergy and clinical immunology,* 77(2), 348-353.

Kelly, J. T., Asgharian, B., Kimbell, J. S., & Wong, B. A. (2004). Particle deposition in human nasal airway replicas manufactured by different methods. Part I: Inertial regime particles. *Aerosol Science and Technology,* 38(11), 1063-1071.

Kelly, J. T., Asgharian, B., Kimbell, J. S., & Wong, B. A. (2004). Particle deposition in human nasal airway replicas manufactured by different methods. Part II: Ultrafine particles. *Aerosol science and technology,* 38(11), 1072-1079.

Liu, Y., Johnson, M. R., Matida, E. A., Kherani, S., & Marsan, J. (2009). Creation of a standardized geometry of the human nasal cavity. *Journal of applied physiology*, 106(3), 784-795.

Mygind, N., & Vesterhauge, S. (1978). Aerosol distribution in the nose. *Rhinology*, 16(2), 79-88.

Na, Kyuhwan, et al. "In vitro nasal mucosa gland-like structure formation on a chip." Lab on a Chip 17.9 (2017): 1578-1584.

Napolitano, A. P., Dean, D. M., Man, A. J., Youssef, J., Ho, D. N., Rago, A. P., . . . & Morgan, J. R. (2007). Scaffold-free three-dimensional cell culture utilizing micromolded nonadhesive hydrogels. *Biotechniques*, 43(4), 494-500.

Pozzoli, M., Ong, H. X., Morgan, L., Sukkar, M., Traini, D., Young, P. M., & Sonvico, F. (2016). Application of RPMI 2650 nasal cell model to a 3D printed apparatus for the testing of drug deposition and permeation of nasal products. *European Journal of Pharmaceutics and Biopharmaceutics*, 107, 223-233.

Pu, Y., Goodey, A. P., Fang, X., & Jacob, K. (2014). A comparison of the deposition patterns of different nasal spray formulations using a nasal cast. Aerosol Science and Technology, 48(9), 930-938.

Rygg, A., Hindle, M., & Longest, P. W. (2015). Absorption and Clearance of Pharmaceutical Aerosols in the Human Nose: Effects of Nasal Spray Suspension Particle Size and Properties. *Pharmaceutical Research*, 33(4), 909-921.

Sander, I. M., Liepert, T. T., Doney, E. L., Leevy, W. M., & Liepert, D. R. (2017). Patient education for endoscopic sinus surgery: preliminary experience using 3D-printed clinical imaging data. *Journal of functional biomaterials*, 8(2), 13.

Sander, I. M., Mcgoldrick, M. T., Helms, M. N., Betts, A., Avermaete, A. V., Owers, E. Leevy, W. M. (2017). Three-dimensional printing of X-ray computed tomography datasets with multiple materials using open-source data processing. *Anatomical Sciences Education*, 10(4), 383-391.

Shah, S. A., Dickens, C. J., Ward, D. J., Banaszek, A. A., George, C., & Horodnik, W. (2014). Design of experiments to optimize an in vitro cast to predict human nasal drug deposition. Journal of aerosol medicine and pulmonary drug delivery, 27(1), 21-29.

Swift, D. L. (1991). Inspiratory inertial deposition of aerosols in human nasal airway replicate casts: implication for the proposed NCRP lung model. *Radiation Protection Dosimetry*, 38(1-3), 29-34.

Wang, Wei, et al. "Live human nasal epithelial cells (hNECs) on chip for in vitro testing of gaseous formaldehyde toxicity via airway delivery." Lab on a chip 14.4 (2014): 677-680.

Warnken, Z. A. C. H. A. R. Y., Kim, Y., Mansour, H., Williams III, R. O., & Smyth, H. D. (2019). Fundamentals in nasal drug delivery. Inhalation Aerosols: Physical and Biological Basis for Therapy, 1.

Zhao, K., & Jiang, J. (2014). What is normal nasal airflow? A computational study of 22 healthy adults. *International Forum of Allergy & Rhinology*, 4(6), 435-446.

Zhuo, C., Lei, L., Yulin, Z., Wentao, L., Shuangxia, W., Chao, W., Dong, D. (2019). Creation and validation of three-dimensional printed models for basic nasal endoscopic training. *International Forum of Allergy & Rhinology*, 0(0), 1-7.

Zhou, Y., Guo, M., Xi, J., Irshad, H., & Cheng, Y. S. (2014). Nasal deposition in infants and children. Journal of aerosol medicine and pulmonary drug delivery, 27(2), 110-116.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

In the preceding detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A nasal simulator comprising:
   a three-dimensional (3D) printed nasal cavity within based on diagnostic imagery of a human nasal cavity;
   a fan system positioned to mimic air flow through the human nasal cavity;
   a first probe access bore formed through the 3D printed nasal cavity to a first location having a first internal contour; and
   an anemometer insert having an outer diameter sized to be slidingly received in and to pneumatically seal the first probe access bore, the anemometer insert having a distal contour that aligns with the first internal contour of the 3D printed nasal cavity, the anemometer insert having a longitudinal bore that is sized to receive a probe of an anemometer to detect characteristics of the air flow through the 3D cavity.

2. The nasal simulator of claim 1, wherein the first probe access bore and the anemometer insert comprise a teeth and groove lock.

3. The nasal simulator of claim 1, further comprising:
   a second probe access bore formed through the 3D printed nasal cavity to a second location; and
   a resting insert having an outer diameter sized to be slidingly received in and to pneumatically seal the second probe access bore, and the resting insert having a distal contour that aligns with the second internal contour of the 3D printed nasal cavity.

4. The nasal simulator of claim 1, further comprising:
   a second probe access bore formed through the 3D printed nasal cavity to a second location; and
   a tissue insert having an outer diameter sized to be slidingly received in and to pneumatically seal the second probe access bore, and the tissue insert having a distal end cavity that receives a tissue insert to form a distal contour that aligns with the second internal contour of the 3D printed nasal cavity.

5. The nasal simulator of claim 4, wherein the tissue insert comprises a gel medium and a nasal tissue sample.

* * * * *